United States Patent [19]

Kumar et al.

[11] Patent Number: 5,388,442
[45] Date of Patent: Feb. 14, 1995

[54] LUBRICATION AND ADHESION TESTING MACHINE

[75] Inventors: Sudhir Kumar, Westmont; James G. F. Cheng, Downers Grove, both of Ill.

[73] Assignee: Tranergy Corporation, Westmont, Ill.

[21] Appl. No.: 959,789

[22] Filed: Oct. 13, 1992

[51] Int. Cl.⁶ .................... G01N 11/14; G01N 19/02
[52] U.S. Cl. ...................... 73/10; 73/53.05; 73/54.28
[58] Field of Search ............. 73/9, 10, 53.05, 53.06, 73/54.28, 54.35

[56] References Cited

U.S. PATENT DOCUMENTS

| | | | |
|---|---|---|---|
| 2,067,996 | 1/1937 | Werder | 73/10 |
| 2,808,563 | 10/1957 | Hornbostel | 73/53.05 |
| 3,033,019 | 5/1962 | Oliver | 73/9 |
| 3,095,730 | 7/1963 | Matheson | 73/9 |
| 3,204,450 | 9/1965 | von Fuchs | 73/53.05 |
| 3,455,145 | 7/1969 | Gustafsson | 73/54.28 |
| 3,777,551 | 12/1973 | Weiss | 73/54.28 |
| 3,823,599 | 7/1974 | Litz et al. | 73/10 |
| 4,458,527 | 7/1984 | McFarland et al. | 73/9 |
| 4,995,197 | 2/1991 | Shieh et al. | 73/9 |
| 5,233,862 | 8/1993 | Longree | 73/10 |

FOREIGN PATENT DOCUMENTS

| | | | |
|---|---|---|---|
| 2194060A | 2/1988 | United Kingdom | 73/53.05 |
| 1516976 | 10/1989 | U.S.S.R. | 73/53.05 |

*Primary Examiner*—Hezron E. Williams
*Assistant Examiner*—George M. Dombroske
*Attorney, Agent, or Firm*—Dorn, McEachran, Jambor & Keating

[57] ABSTRACT

A new machine for laboratory testing of lubricants and tractive/braking characteristics commonly known as adhesion has been designed. It can provide measures of lubricant performance characteristics of lubricity and durability (retentivity). Furthermore, it provides a continuous description of lubricant consumption characteristics after application of fresh lubricant. The machine uses two suitably profiled and loaded wheels robing against each other with one wheel powered and the other wheel either freely rolling or braked. The axes of the two wheels can be kept aligned or misaligned by a specified angle for testing of lubricants or adhesion. For making the machine more accurate and usable a quick engagement self-aligning compound shaft and wheels have been designed. A three point alignment base with two linear slides, spline connection and drive shaft are used for setting the null condition. The machine uses a feedback speed control electric motor for maintaining a constant speed of the wheel which is critical for the testing. Power measured is analyzed through a computer or microprocessor which plots the lubrication characteristics in graphical form. For accurate measurement of adhesion a special load cell arrangement for cancellation of reaction moment has been designed in the machine. Adhesion and creep (nondimensional wheel slip) are also measured and plotted through the computer.

17 Claims, 10 Drawing Sheets

LUBRICATION AND ADHESION TESTING MACHINE

BACKGROUND OF THE INVENTION

Figure 1A:
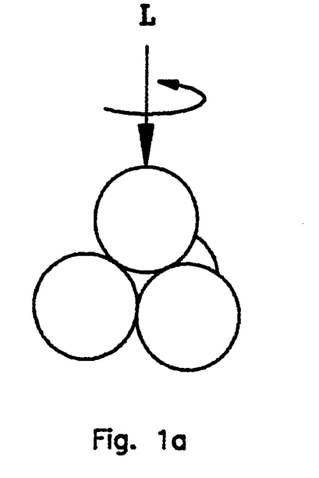
Figure 1B:
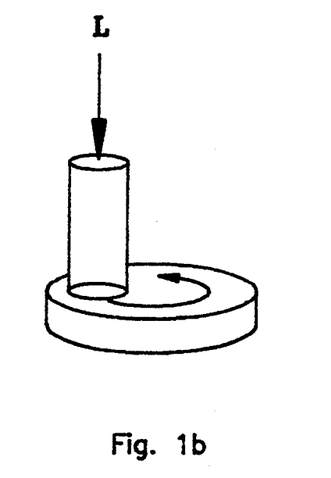
Figure 1C:
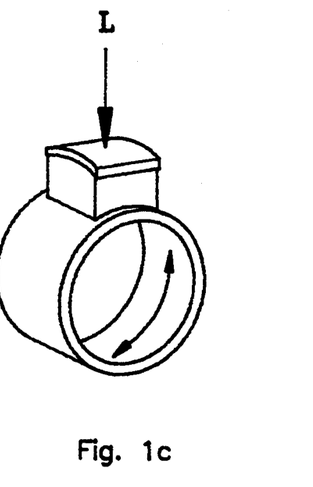
Figure 1D:
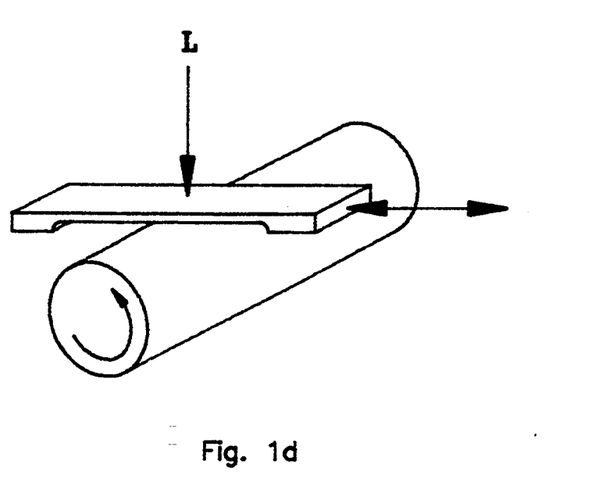
Figure 1E:
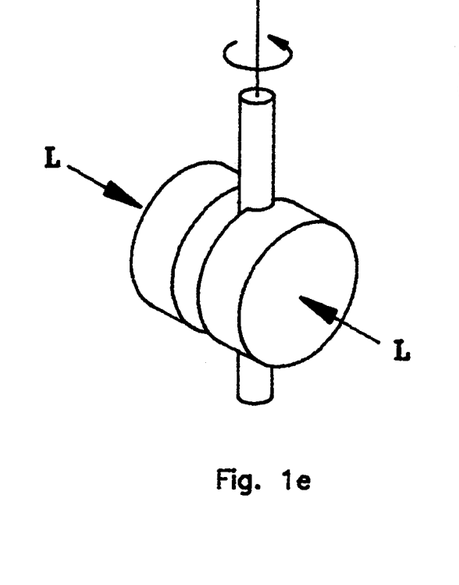
Figure 1F:
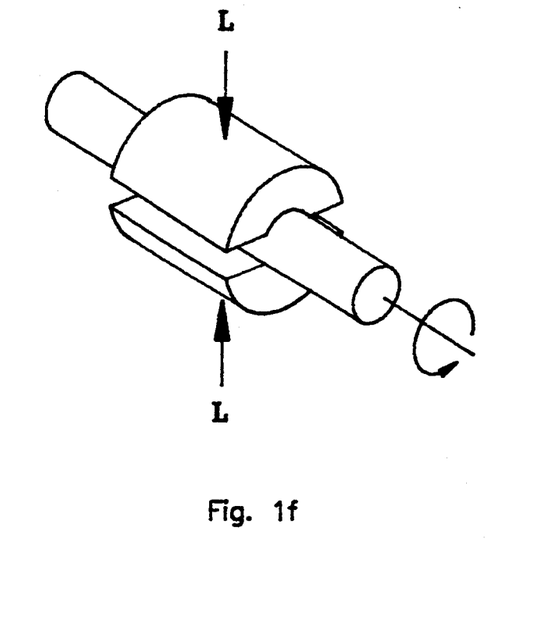
Figure 1G:
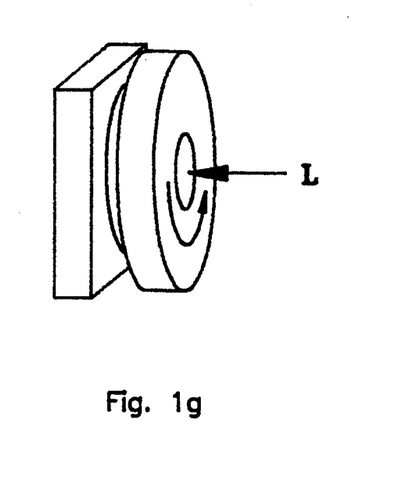
Figure 1H:
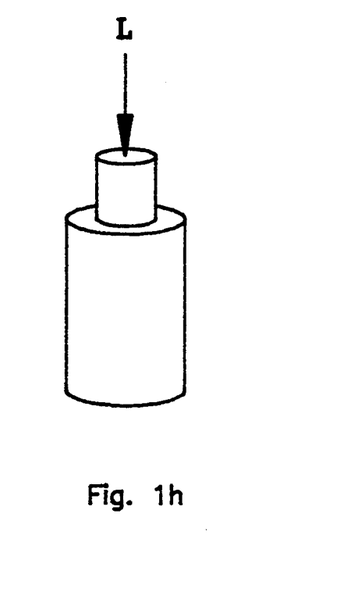

This invention deals with a new machine for laboratory testing of lubricants and tractive/braking characteristics commonly known as adhesion. There is an important need at present to determine lubricant performance characteristics of lubricity, durability or retentivity and a continuous history of the lubricant degradation which was not fulfilled by the various machines available in the past. There are a large number of wear/lubrication testing machines that have been commonly used to characterize the anti-wear and extreme pressure performance of lubricants. FIG. 1 shows a variety of friction and wear test methods as cited by Lancaster (1). The four ball test (FIG. 1a) is very commonly used in determining the wear resistance of a lubricant in tests such as that described by ASTM D2266 (Four Ball Wear Test). This test is also used to evaluate extreme pressure characteristics by using tests such as: ASTM D2596 (Four Ball EP Test). The pin/disk configuration (FIG. 1b) is used for wear testing. The block/ring configuration (FIG. 1c) is used to determine extreme pressure properties in tests such as ASTM D2509 (Timken Test). The reciprocating pad on ting arrangement is used for friction and wear measurements (FIG. 1d). The Falex conforming contact test (FIG. 1e) or pin and vee block test is useful in determining the frictional properties of lubricant films and solid additives. The journal bearing (FIG. 1f) and the thrust bearing (FIG. 1g) are used for bearing lubrication tests. The press fit configuration (FIG. 1h) is used for testing solid films and dry powders.

The above tests generally provide either a pass or fail result for a lubricant, or a single, value for the failure of the lubricant at the end of the test. Kumar and his students tested a two wheel roller test rig for testing wear and lubricants. This machine provided good rolling wear data and with considerable difficulty provided approximate lubrication test data on lubricity and durability. It could not measure adhesion and creep successfully. The present invention is capable of performing accurate advanced and automated with full computer interface lubrication as well as adhesion tests as a result of significant new concepts and design features. This is performed with great convenience and accuracy.

SUMMARY OF THE INVENTION

In order to make a table top roller rig for testing of lubricants and adhesion/creep, usable, practical and accurate, a number of mechanical design and computer utilization innovations made to make the rig commercially acceptable, constitute the present invention of the new testing machine.

In order to avoid the difficult and time-consuming process of the rolling wheel mounting and aligning on the shafts, a quick engagement self-aligning compound shaft and wheels have been invented. A three point alignment base with two linear slides suitable for use in the lubrication testing machine was designed to improve performance and economics.

A special load cell arrangement for cancellation of reaction moment for purity of adhesion measurement has been designed for use with a brake on a small wheel roller rig so that reliable values of adhesion can be obtained on a table top roller rig. This has not been possible before. A new design and method for setting the null condition for the new lubrication adhesion testing machine was developed. This is quite critical for accurate and repeatable testing of lubrication and adhesion. The method involves making the lateral force produced by the two wheel contact zero as measured by no lateral movement of the Wheel base on linear slides using a spline connection on the drive shaft. The base is constrained by a two slot guide and screws arrangement so that the lateral movement is kept within design limits.

For reliable determination of power consumed in the rolling contact a feed back speed control DC motor using a digital speed indicator was developed. Use of such a system is very helpful in automatically keeping the motor speed constant which is essential for lubrication testing.

Determination of electrical power consumed by the D.C. motor is made by measuring voltage and current readings many times each second, averaging them and multiplying them. This determination of power enables determining several important features of lubricant testing. These include: determination of motor power stabilization, reduction of power consumed when lubricant is applied, and test completion stage assessment. The invention also deals with automatic determination and plotting of adhesion and creep through use of computer software.

BRIEF DESCRIPTION OF THE DRAWINGS

FIGS. 1A—1A show some current wear/lubrication testing methods described as: 1A four ball; 1B pin on disk; 1C block on ring; 1D reciprocating pad on ring; 1E Falex conforming contact; 1F journal bearing; 1G thrust bearing; and 1H press fit. L indicates the load applied on the sliding components of each machine.

FIG. 2 shows the basic concept of the test machine. Two model wheels 10 and 11 roll against each other with one wheel 11 powered and the other either freely rolling or braked by a brake. The profiles of the two wheels are calculated to produce the needed stress distribution. An angle 12 is developed between the axes of the two wheels for conducting lubrication test. For the adhesion test this angle is zero or any value as desired.

DETAILED DESCRIPTION OF THE INVENTION

As discussed earlier, there are no machines available to date which provide a good continuous description of lubricant consumption characteristics and its initial lubricity. There is also no small or inexpensive machine available today which can measure adhesion and creep of tractive or braking wheels. In addition, computer data acquisition and control of such a machine for lubricant testing and/or adhesion testing has not been done. The present machine accomplishes the above making the press of such testing much easier and accurate.

Figure 2:
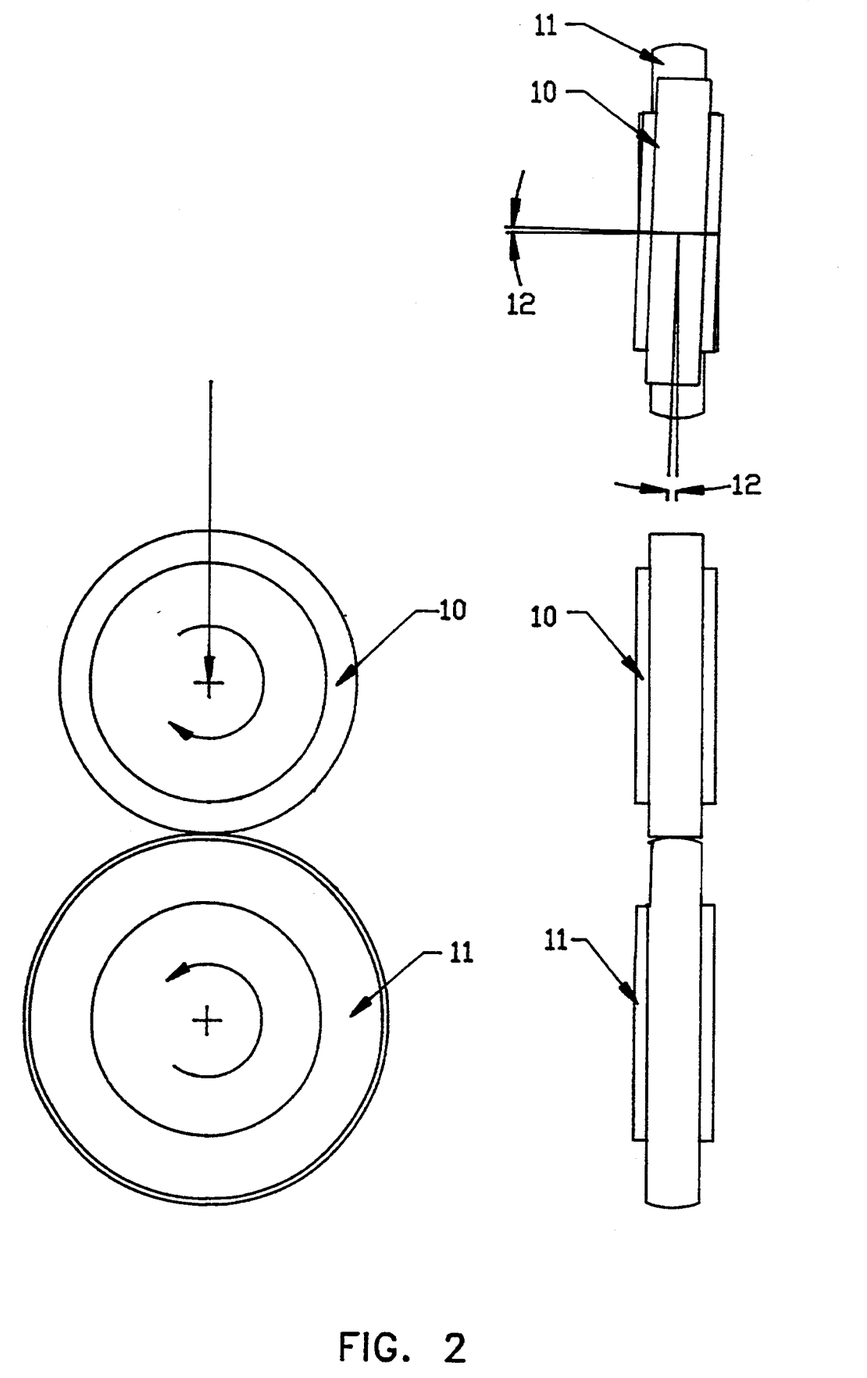

The basic concept of testing with this machine is shown in FIG. 2. Two wheels 10 and 11 are rolling against each other with one wheel 11 powered and the other either freely rolling or braked by a braking device such as an air brake or a motor/generator. The two wheels are profiled to produce the contact stress of the field condition being simulated in the laboratory for a load calculated by theory of elasticity.

For lubricant testing, the axes of the two wheels are purposely misaligned by an angle which produces the slip rate of the field condition in which the lubricant is used. After application of a small quantity (many microliters) of the lubricant in the wheel contact area, the power changes in the motor become a measure of the performance of the lubricity and durability (also called retentivity) of the lubricant.

For adhesion testing one wheel is powered while the other is braked. The braking force between the wheels and the microslip (a nondimensional value) describe the adhesion creep characteristics of the two wheel contact under the contamination condition of the surface.

Figure 3:
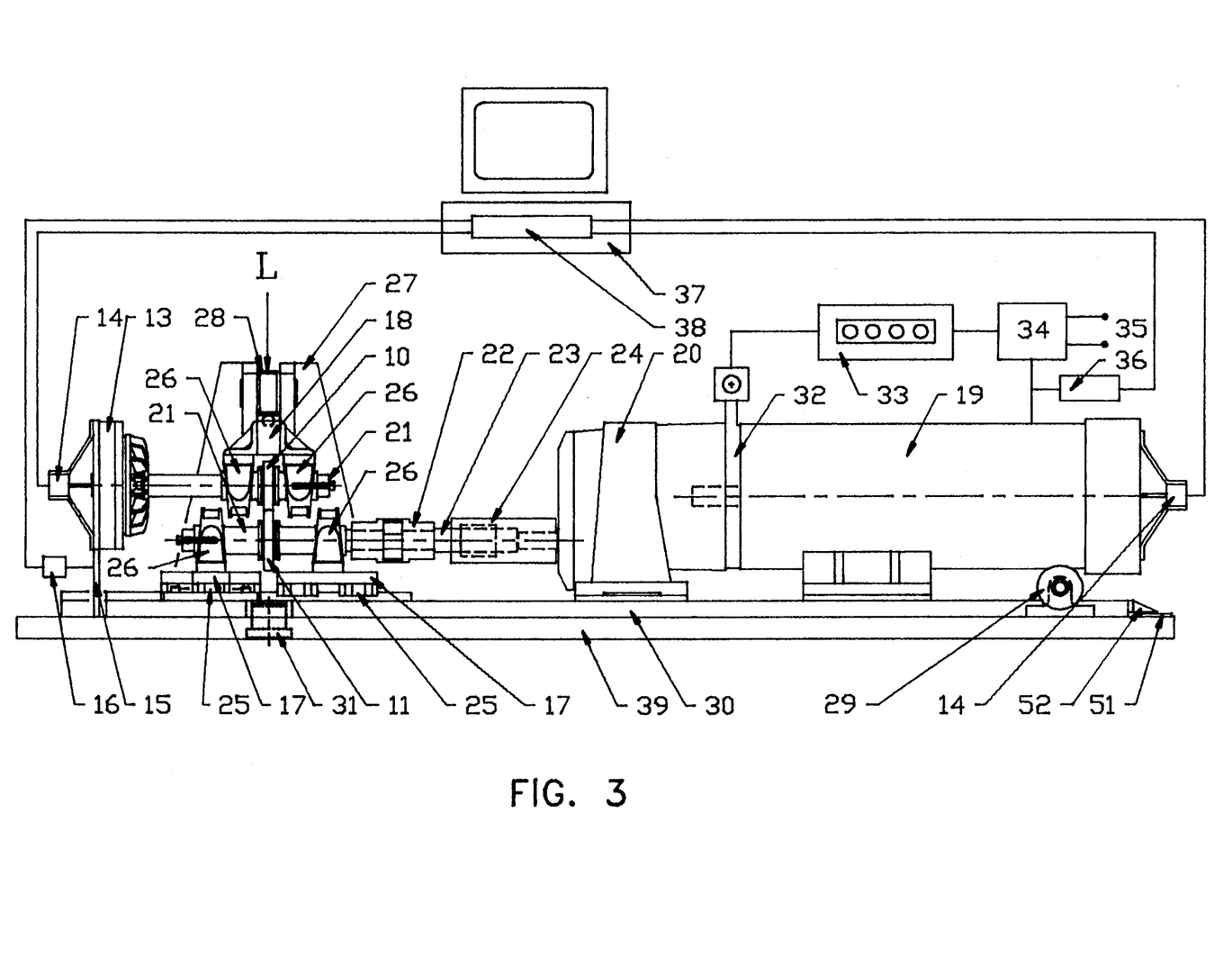
FIG. 3 shows a schematic diagram of the lubrication adhesion testing machine with the motor feedback control and computer data acquisition system.

FIG. 3 shows a schematic of the new machine with the new features which now make the machine commercially usable and accurate for lubricant testing. It is the first such machine for adhesion testing. The figure shows the version of the machine which can test lubricants as well as conduct adhesion-creep tests. If only lubricant tests are done, one would do without the brake 13, the shaft encoders 14, the braking torque load cell 15, and the signal conditioner 16. The two wheels are mounted with the help of special design compound shafts 21 for quick and easy replacement of wheels, without the need of complicated dismantling and aligning procedures that would be needed otherwise. Wheel 10, experiences a braking torque with the brake 13. The lower wheel 11 is driven by a DC electric motor 19 through a gear reducer 20, a spline beating 24, a spline shaft 23, and a flexi-coupling 22. The whole assembly of the lower wheel is mounted on a stiff plate 30 which can swivel around a pivot 31 which is mounted in the base plate 39. The pivot 31 is located accurately below the contact point of wheel 10 and wheel 11. Wheel 10 is mounted in a swinging cantilever-type carriage 18. The cantilever can rotate in a vertical plane about a horizontal pin mounted in a support column 27. The loading of the cantilever carriage is performed through a cantilever beam 28 which carries a requisite load at the end of the beam away from the support column 27. The wheels 10 and 11 can rotate freely while carrying lateral and vertical loads through thrust beating pillow blocks 26. The lower two thrust bearing pillow block are supported on special support plates 17 which can move laterally on linear bearings 25. The motor speed is controlled accurately at a constant specified RPM through a special feedback electronic control system. The electronic control system consists of a speed sensor 32, a speed controlling unit 33, and a DC power source 34.

The power is converted from an AC source 35 to DC by a conversion unit 34 for powering the DC motor 19. Special electronics 36 for measuring the voltage, current, or wattage used in the motor 19 is utilized to provide input to the computer 37 through an I/O card 38. This card also receives other inputs of rotational speeds through sensors 14 and braking torque load cell 15.

Figure 4:
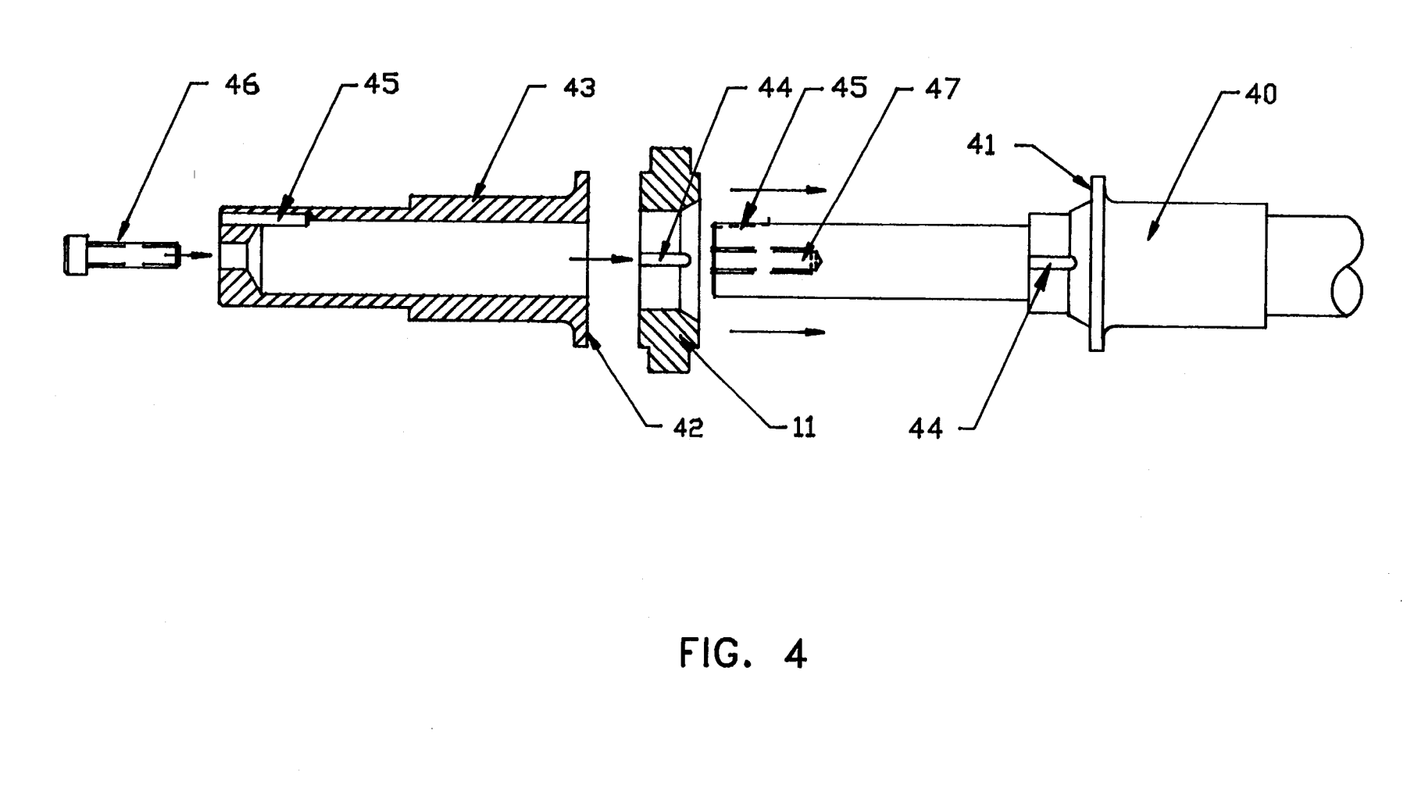
FIG. 4 shows a new design of a quick engagement self aligning compound shaft and wheels.
Figure 5:
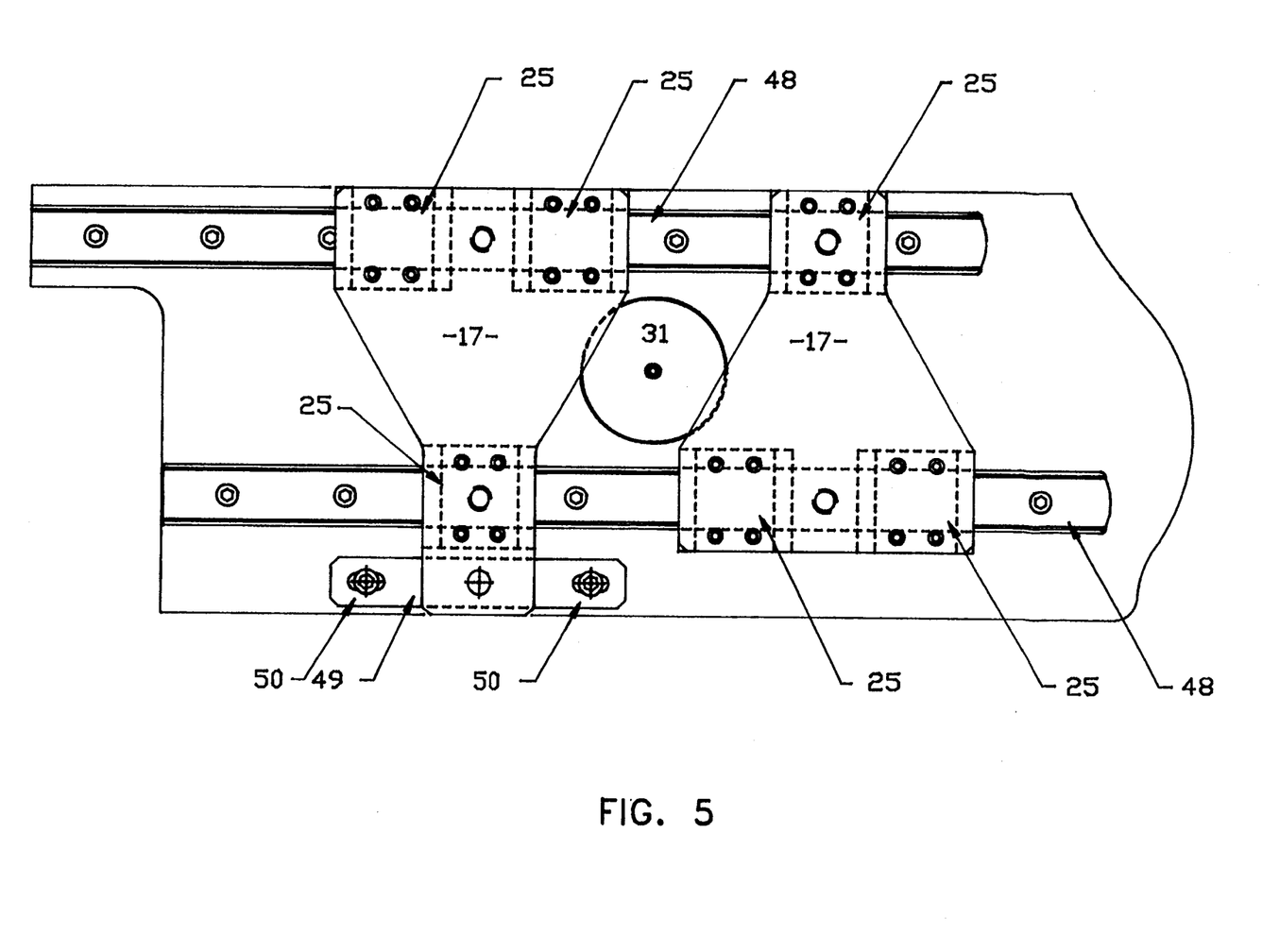
FIG. 5 shows two three-point-support carriages on two linear bearing slides along with a linear movement limiting lock.
Figure 6:
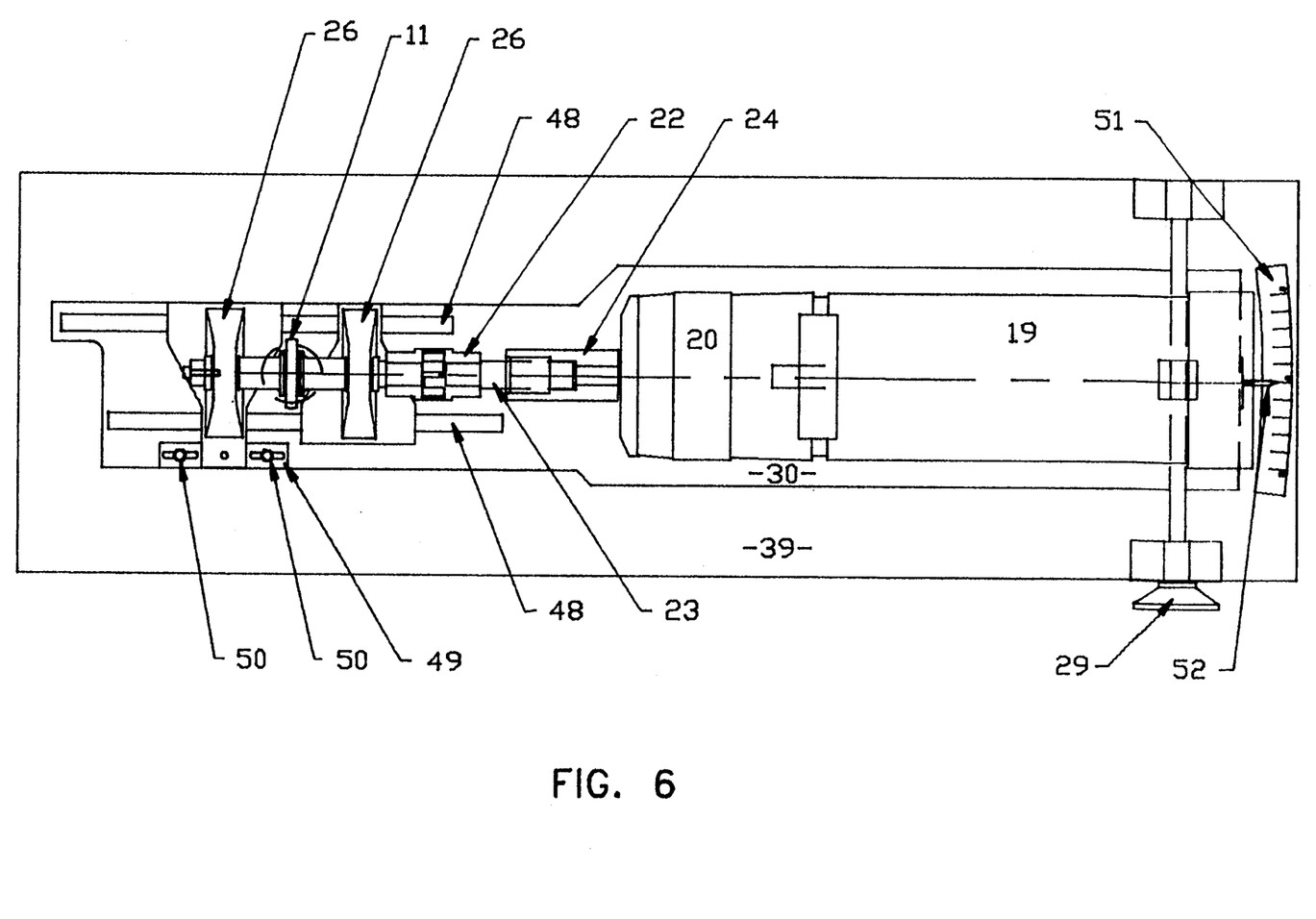
FIG. 6 shows the top view of the design elements used in setting the null condition for starting the experiment. These are linear slides, linear displacement limiting and locking bar, spline shaft and spline bearing.

The above machine incorporates several innovations which make it a unique roller rig testing machine for lubricants and adhesion. It is very important that the model wheels be mounted in perfect alignment radially, laterally, and wobble-free. This requirement makes the replacement of test wheels and operation of the roller test rig very time consuming, difficult, and dependent on operator skill. A new compound shaft shown in FIG. 4 has been invented to replace the model wheels quickly and easily while providing automatic alignment of the wheel and not requiring special operator skills. This compound shaft consists of two parts 40 and 43, which when assembled together sandwich the wheel 11 between the shoulders 41 and 42. The wheel seats itself with good alignment automatically on the conical base of the shoulder 41. It is locked in place by a key which is fitted in the keyway 44, partly on the wheel and partly on the shaft 43. The diameter of the shaft 40, which fits in the inside cavity of shaft 43, has very close tolerance. The two shafts are secured to each other by tightening the screw 46 in the threaded cavity 47. As shown in FIG. 5 the whole compound shaft system is supported on two sliding base plates 17 mounted on two linear slides 48 with linear bearings 25. This facilitates the separation of the compound shaft by simply sliding shaft 43 away from shaft 40 by moving apart the sliding bases 17. The top wheel compound shaft 26 is opened up by unscrewing several screws holding the top wheel carriage 18 together. During normal operation the slide system is locked in position by the locking bar 49 and the tightening screws 50. This locking and slide system is also very valuable in setting the null position (zero angle of attack of the two wheels) of the machine before starting an experiment. This is shown in FIG. 6 in which only the lower wheel 11 is shown mounted on the swiveling plate 30 along with the linear slides 48 and the drive system 19, 20, 22, 23, and 24. The null position is established by operating the wheels 10, 11 while keeping screws 50 loose. The angle shown on the angle scale 51 controlled by the screw/knob 29 should be selected such that the wheel carriage 26 does not slide in either direction on slides 46 even though the screws 50 are loose. This is permitted by using a spline shaft 23 with a spline bearing 24 and a flexi-coupling 22. The lateral movement of the locking bar 49 is limited in either direction by the length of the slots in the locking bar 48 through which the screws 50 are loosely fastened. Accurate setting of the null position obtained in this fashion is very critical for conducting a reliable and repeatable experiment. It is nearly impossible to set this null position so accurately by conventional mechanical alignment methods.

Figure 7:
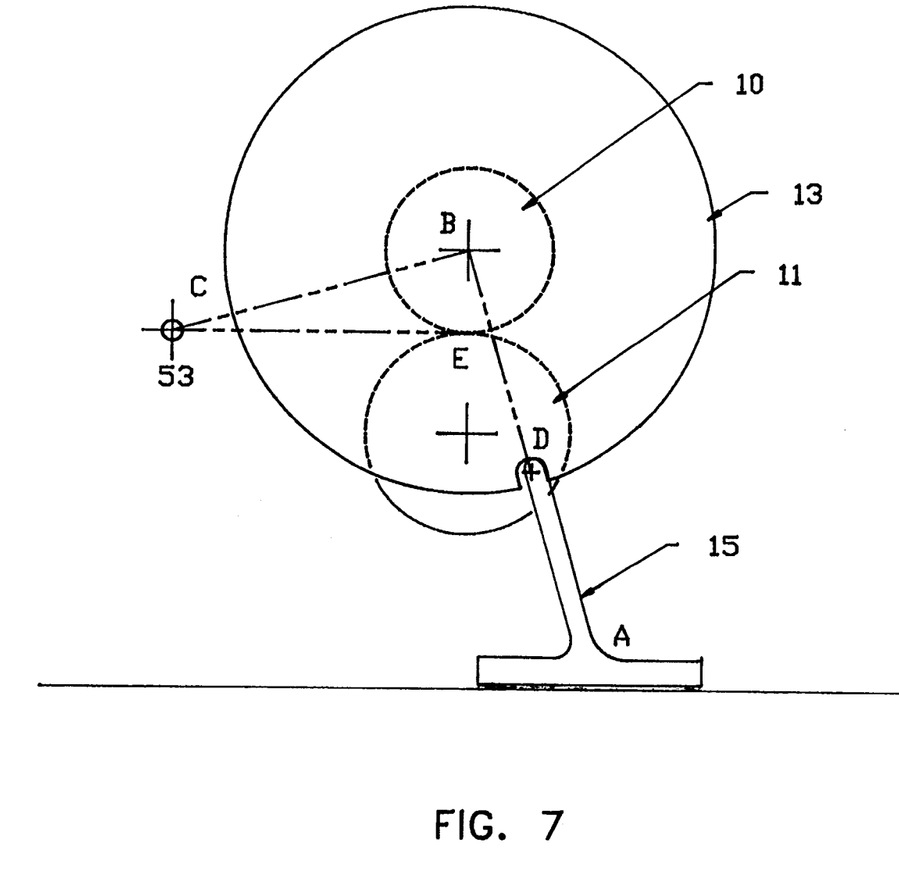
FIG. 7 shows a side schematic of the arrangement of the load cell restraining the brake so that the friction force and the reaction force moments are made zero to keep the adhesion force reading by the load cell correct.

For measurement of adhesion between the two wheels 10 and 11, shown in FIG. 7, a special arrangement of the load cell 15 has been invented. This special arrangement positions the load cell 15 at an angle pointing through the axis B of wheel 10 so that line BC which is perpendicular to line AB goes through the center of pivot 53 of the support of the top wheel 10. The load cell 15 restricts the movement of the brake 13 mounted on the shaft of wheel 10, through a slot in the brake at position D. The tangent at the wheel contact E must also pass through the center of the pivot 53 which coincides with position C. With this arrangement the reaction moments which alter the adhesion values measured are completely canceled and the purity of adhesion measurement is maintained.

Figure 8:
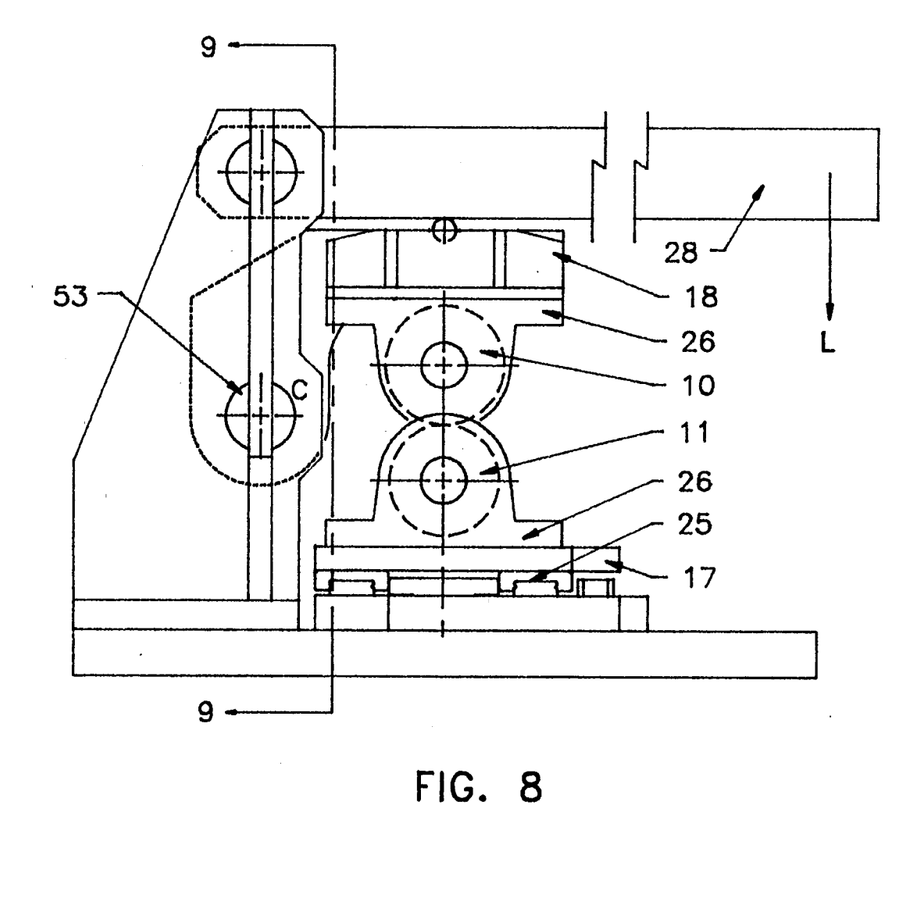
FIG. 8 shows a side view of the machine showing the support column, cantilever type top wheel carriage, and a view of section A—A.

The above requirement of FIG. 7 is satisfied by the design features shown in FIG. 8. It shows the side view of the machine including the support column 27, cantilever type carriage 18, and pivot 53 (axis C) about which the carriage rotates. The figure also shows the cantilever beam 28 which applies the load to the top wheel through the carriage. The bearing pillow blocks 26, top wheel 10, bottom wheel 11, linear beatings 25, and support plates 17 are also shown.

Figure 9:
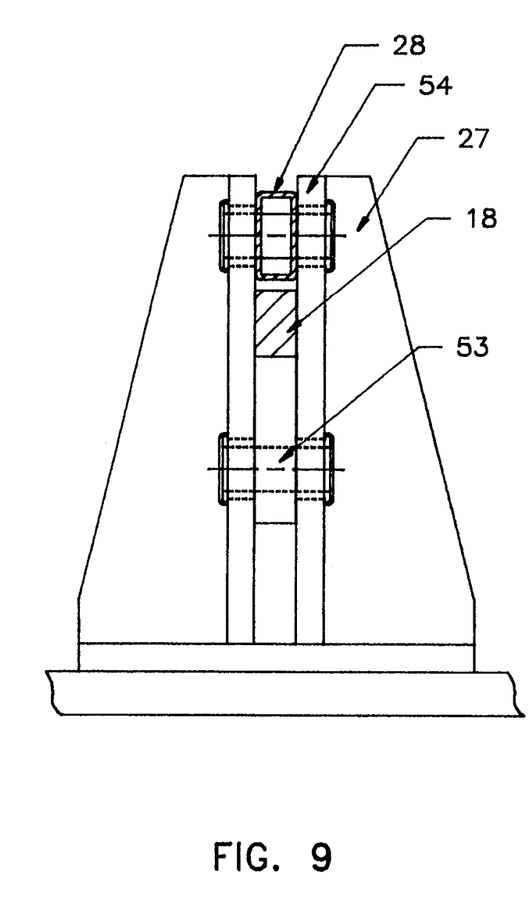
FIG. 9 shows a view of section 9—9 in FIG. 8.

View 9—9 of this machine is shown in FIG. 9. The support column arrangement and the cantilever type carriage connection with the pin 53 (axis C) are also shown in this view. The cantilever carriage may be supported by a single heavy plate 18 which pivots on the pin 53 between the support column elements 54. The carriage may also be supported alternatively on pin 53 outside the support columns members 54, not shown in FIG. 9.

Accurate determination of the power consumed in the rolling contact can be performed only when the speed of the motor is kept constant. For this purpose an electronic feedback speed control system was developed and utilized. This feedback loop is shown in FIG. 3 with the speed sensor 32, speed control 33, DC power source 34 connected in a loop with the DC motor 19. The motor speed is selected by the operator through the speed controller 33. The motor speed is displayed on the speed controller 33. The motor speed can be specified by the operator. This digital motor speed control system ensures the accuracy of test results of this machine.

The electrical power consumed by the DC motor is determined by measuring voltage and current readings and sampling them through software at an operator specified rate, averaging them and multiplying the two quantities. The power may alternatively be measured with a watt meter which provides an input to the computer or microprocessor. This power determination is very important for establishing different stages of lubricant testing. These stages are: the motor power consumption during the dry contact condition, the condition of motor power stabilization, increase of motor power consumed when an angle of attack is developed between the two model wheels, reduction of power consumed after application of lubricant in the wheel contact area, and return of motor power consumption to the level corresponding to the dry contact condition. These stages describe the lubricant performance in the test.

This invention also deals with automatic determination and plotting of adhesion and creep characteristics of two wheel surfaces by the use of computer data acquisition. Adhesion is determined by measuring the wheel friction force through the load cell 15 and dividing it by the vertical load L applied through the loading bar 28. The creep is determined by measuring the slip between the two wheels with the help of the optical shaft encoders 14 and dividing it by the wheel speed. The computer software is used to display these characteristics in graphical form.

We claim:

1. A test stand for lubricant and/or adhesion testing, comprising:
   a plate having first and second bearings supporting a first shaft for rotation, the bearings being slidably mounted for axial translation on the plate;
   drive means for driving the first shaft;
   coupling means for connecting the drive means and first shaft in driving engagement, the coupling means allowing axial adjustment of the relative positions of the first shaft and drive means;
   a first wheel mounted on the first shaft for rotation therewith;
   support means for a second shaft and wheel rotatable thereon, the second wheel being in contact with the first wheel.

2. The test stand of claim 1 wherein the first shaft and drive means have splines formed thereon and the coupling means comprises a spline coupling engageable with the splines of the first shaft and drive means.

3. The test stand of claim 1 further comprising a pair of parallel tracks attached to the plate, first and second support plates attached to linear bearings which ride on the tracks, the first and second bearings being mounted on the first and second support plates, respectively.

4. The test stand of claim 3 further comprising a locking bar connected to at least one of the support plates for adjustably fixing said support plate in a particular position on the tracks.

5. The test stand of claim 1 wherein said first shaft is a compound shaft having two halves engageable in telescoping relation.

6. The test stand of claim 5 wherein one of said shaft halves is supported in the first bearing and the other shaft half is support in the second bearing such that one of said bearings can be axially translated while the other remains stationary.

7. The test stand of claim 5 further comprising releasable locking means for fixing the compound shaft halves together.

8. The test stand of claim 1 wherein the support means comprises a support column, a support arm attached to the column and extending to a point above the first wheel, and bearing means attached to the support arm for rotatably supporting the second shaft.

9. The test stand of claim 8 wherein the support arm is pivotally connected to the support column.

10. The test stand of claim 9 wherein the pivot point of the support arm and support column is located in the same horizontal plane as the contact point of the two wheels.

11. The test stand of claim 10 further comprising a brake engageable with the second shaft, and a load cell engageable with the brake and aligned such that a line through the load cell intersects the center of the second wheel and is perpendicular to a line connecting the center of the second wheel to the pivot point of the support arm and support column.

12. The test stand of claim 8 further comprising a cantilevered load arm pivotally connected to the support column and engageable with the support arm to apply a load thereto.

13. The test stand of claim 1 further comprising a base member disposed underneath the plate, the plate being pivotally connected to the base member, the support means being mounted on the base member such that the plate and first shaft cannot be rotated relative to the support means and the second shaft.

14. The test stand of claim 1 wherein the drive means is an electric motor and further comprising means for measuring the voltage and current used in the motor.

15. In a test stand for lubricant and/or adhesion testing, an improved method of setting up the stand for operation, comprising the steps of:

mounting a swivel plate for angular rotation on a base member;

mounting a first wheel and shaft combination for rotation and for adjustably fixed axial translation on said swivel plate;

mounting a second wheel and shaft combination on the base member for rotation in contact with the first and second wheels in contact with each other;

driving at least one of said first or second wheels while permitting axial translation of said first shaft;

adjusting the angular position of the swivel plate such that the first shaft does not move axially; and fixing the axial position of the first shaft and the angular position of the swivel plate.

16. The method of claim 15 further comprising the step of providing a axially adjustable connection between said first shaft and a means for driving the wheels.

17. A test stand capable of performing lubricant and/or adhesion testing, comprising a base member, a support plate mounted on the base member and pivotable about a pivot point, a first wheel and shaft mounted for rotation on one of the support plate or base member, a support carriage mounted on the other of the support plate or base member and having a second shaft and wheel mounted for rotation thereon, the second wheel being in contact with the first wheel with the point of contact being aligned with the pivot point, drive means mounted on one of the support plate or base member for driving the one of the shafts also mounted thereon, a brake engageable with the other shaft, and a load cell engageable with the brake.

* * * * *